US005945271A

United States Patent [19]
Cohen

[11] Patent Number: 5,945,271
[45] Date of Patent: Aug. 31, 1999

[54] ARTIFICIAL MEDIA FOR REARING ENTOMOPHAGES COMPRISING STICKY, COOKED WHOLE EGG

[75] Inventor: Allen C. Cohen, Starkville, Miss.

[73] Assignee: The United States of America as represented by the Secretary of Agriculture, Washington, D.C.

[21] Appl. No.: 09/094,158

[22] Filed: Jun. 8, 1998

Related U.S. Application Data

[63] Continuation-in-part of application No. 08/699,815, Aug. 19, 1996, Pat. No. 5,834,174.
[51] Int. Cl.$^6$ .............................. A01N 1/02; A01K 29/00
[52] U.S. Cl. .......................... 435/1.1; 435/348; 435/390; 435/391; 119/6.6; 424/407
[58] Field of Search ........................... 435/1.1, 348, 390, 435/391; 119/6.6; 424/407

[56] References Cited

PUBLICATIONS

A.C. Cohen, "Simple Method for Rearing The Insect Predator *Geocoris Punctipes*(*Heteroptera: Lygaeidae*) on a Meat Diet," *Journal of Economic Entomology* 78:1173–1175 (1985).
A.C. Cohen and N.M. Urias, "Meat–Based Artificial Diets for *Geocoris Punctipes* (Say)," *The Southwestern Entomologist* 11:171–176 (1986).
A.C. Cohen and R.T. Staten, "Long–Term Culturing and Quality Assessment of Predatory Big–Eyed Bugs, *Geocoris punctipes*," in *Applications of Genetics to Arthropods of Biological Control Significance*, (Eds.) S.K. Narang et al., CRC Press Inc, Boca Raton, Chapter 7, pp. 121–132 (1994).
A.C. Cohen and N.M., Urias, "Food Utilization and Egestion Rates of the Predator *Geocoris Punctipes* (*Hemiptera: Heteroptera*) Fed Artificial Diets with Rutin," *Journal Entomol. Sci.* 23:174–179 (1988).
P. De Clercq and D. Degheele, "A Meat–Based Diet for Rearing the Predatory Stinkbugs *Podisus Maculiventris* and *Podisus Sagitta* [Het.:*Pentatomidae*]," *Entomophaga* 37:149–157 (1992).
A.C. Cohen, "Using a Systematic Approach to Develop Artificial Diets for Predators," in *Advances in Insect Rearing for Research and Pest Management*, (Eds) T.E. Anderson and N.C. Leppla, Westview Press Inc., Boulder, Chapter 6, pp. 77–91 (1992).

S. Grenier, P.D. Greany and A.C. Cohen, "Potential for Mass Release of Insect Parasitoids and Predators Through Development of Artificial Culture Techniques," in *Pest Management in the Subtropics Biological Control—A Florida Perspective*, Intercept Ltd., P.O. Box 716, Andover, Hampshire, SP10 1YGUK, Chapter 10, pp. 181–505 (1994).
J.L.D. Saavedra, J.C. Zanuncio, R.N.C. Guedes and P.De Clercq, "Continuous Rearing of *Podisus Nigrispinus* (Dallas) (*Heteroptera: Pentatomidae*) on and Artificial Diet," *Med. Fac. Landbouww. Univ. Gen.* 61(3a):767–772 (1996).
P. Singh and H.L. House, "Antimicrobials: 'Safe' Levels in a Synthetic Diet for an Insect, *Agria Affinis*," *Journal of Insect Physiol.* 16:1769–1782 (1970).
J. DeBolt, "Meridic Diet for Rearing Successive Generations of *Lygus hesperus*," *Annals of the Entomological Society of America* 75(2):119–122 (1982).
J.C. Zanuncio, J.L.D. Saavedra, H.N. Oliveira, D. Degheele and P. DeClercq, "Development of the Predatory Stinkbug *Brontocoris tabidus* (Signoret) (*Heteroptera: Pentatomidae*) on Different Proportions of an Artificial Diet and Pupae of *Tenebrio molitor* L. (*Coleoptera: Tenebrionidae*)," *Biocontrol Science and Technology* 6:619–625 (1996).
A. Bratti, "In–Vitro Rearing Techniques for *Entomophagous Parasitoids*," *Boll.. Entomol. Univ. Stud. Bologna* 44:169–220 (1990).
T.J. Henneberry and A.C. Cohen, "Mass–Reared Insects Get Fast Food," *Agricultural Research* pp. 4–7 (Jun. 9, 1997).

*Primary Examiner*—Sandra E. Saucier
*Attorney, Agent, or Firm*—M. Howard Silverstein; John D. Fado; Margaret A. Connor

[57] ABSTRACT

An improved artificial diet or growth medium for rearing entomophages (predatory arthropods and parasitic insects). The diet also finds use as a bait and feeding stimulant for entomophages, and as use as a supplement for artificial diets for phytophagous pests that also display some insect consumption. The growth medium is composed of a mixture of (a) an adherent, fibrous retention substrate, (b) a protein-lipid paste, and (c) a liquid, and provides nutrients in a stabilized form in amounts and proportions effective to support growth of entomophages. An exemplary formulation is a mixture of adherent, fibrous cooked whole egg, ground beef and beef liver protein-lipid paste, and water. The growth medium is suitable for mass production of entomophages at a reasonable cost for use as biological control agents, and is well suited for rearing entomophages that feed by the process of extra-oral digestion.

10 Claims, No Drawings

ARTIFICIAL MEDIA FOR REARING ENTOMOPHAGES COMPRISING STICKY, COOKED WHOLE EGG

This application is a continuation-in-part of application Ser. No. 08/699,815, filed Aug. 19, 1996 now U.S. Pat. No. 5,834,177. The prior application is hereby incorporated herein by reference.

BACKGROUND OF THE INVENTION

1. Field of the Invention

The present invention relates to an improved artificial diet or growth medium for rearing entomophages (predatory arthropods and parasitic insects). The growth medium of the invention is suitable for mass production of entomophages at a reasonable cost for use as biological control agents. The diet also finds use as a bait and feeding stimulant for entomophages, and as use as a supplement for artificial diets for phytophagous pests that also display insect consumption.

2. Description of the Art

In the United States and throughout the world, the application of synthetic chemical insecticides is the primary method of controlling insect pests of many agricultural commodities, including food, fiber, and ornamental crops. However, there is an increasing interest in reducing the use of chemical pesticides and fertilizers and to make agriculture more sustainable. Biological control is recognized as the best alternative to the use of chemical insecticides for controlling insect pests.

A major stumbling block to using biological control on a large scale as an alternative to pesticides is that it has been impossible to produce adequate numbers of predatory insects to effect reduction of large outbreaks of pest populations. For example, arthropod predators and parasites have been used successfully for decades to control insect pests, however, the scale of their use has been limited because of inadequate methods to artificially produce these predatory insects. Thus, one of the greatest needs in the field of biological control of insects is the mass production an insect's natural enemies at a reasonable cost. However, despite intensive research for many years on artificial media suitable for rearing predatory insects, it is still necessary to rear these beneficial insects on their natural hosts/prey or on unnatural factitious hosts. These classical methods are too expensive to allow large scale use of beneficial insects in commercial agriculture.

The scientific literature has reported that the feeding behavior of predatory insects involves feeding on hemolymph and/or body fluids from impaled prey. For example, it has been reported that the larvae of nearly all neuropterans, which includes some of the most important families in biological control, such as Chrysopidae (green lacewings) and Hemerobiidae (brown lacewings), which attack many agricultural pests, including whiteflies, aphids, scale insects, and mealy bugs, possess long curved mandibles which act like forceps to grasp and pierce the prey and suck out the body fluids (See P. Debach, *Biological Control by Natural Enemies*, Cambridge University Press, page 40 (1974). Further, on page 43, Debach shows the predatory big-eyed bug Geocoris, another predatory insect useful for biocontrol of important economic crop insects, sucking body fluids of its prey through its proboscis. Thus, the predator feeding models in the literature suggested that the best artificial medium for these "liquid feeders" should have a liquid form. E. S. Vanderzant, *Journal of Economic Entomology* 66:336–338 (1973) and S. A. Hassan and K. S. Hagen, *Zeitschrift fur angewandte Entomologie*, 86:315–320 (1978) report liquid diets for rearing *Chrysopa carnea* Stephens (lacewings) larvae. More recently, semi-solid meat-based artificial diets have been described for rearing *Geocoris punctipes* (Say) (A. C. Cohen *Journal of Economic Entomology*, 78:1173–1175 (1985); A. C. Cohen and N. M. Urias, *The Southwestern Entomologist*, 11:171–176 (1986); A. C. Cohen and R. T. Staten in *Applications of Genetics to Arthropods of Biological Control Significance*, Eds. S. K. Narang et al., CRC Press, Inc., Chapter 7, pp. 121–132 (1994)).

The importance and need to mass produce an insect's natural enemies at a reasonable cost for biocontrol is discussed in the review article by S. Grenier et al. in *Pest Management in the Subtropics, Biological Control—a Florida Perspective*, Eds. D., Rosen, F. D. Bennett, and J. L. Capinera, Intercept Press, Andover, U.K., Chapter 10, pp. 181–205 (1994). The authors present a review of over a half century of research on development of artificial media for entomophages, and report successes in producing media for ectoparasitoids and predators. However, in spite of the importance of predatory insects as biological control agents for economically important insect pests, none of these artificial media has found its way into use in the commercial production of any entomophage, and none of these media have been incorporated into the augmentative production systems for these predators. Thus, production of these beneficial insects still involves the costly method of rearing them on their natural hosts/prey or on unnatural factitious hosts. For the production of the generalist predator, *C. Carnea* (lacewing), the current cost is about $500 per kg. As is clear from the foregoing, the use of predatory insects as biological control agents in commercial agriculture depends on the development of mass rearing technology at reasonable cost.

SUMMARY OF THE INVENTION

The present invention is directed to an improved artificial diet or growth medium for providing nutrients effective for rearing entomophages. The invention also finds use as a bait and feeding stimulant for entomophages. The growth medium of the invention also finds use as a supplement for artificial diets for phytophagous pests that are known to supplement their plant-eating habits with some insect consumption.

The artificial growth medium is composed of a mixture of (a) a sticky, stringy network, hereinafter denoted as an adherent, fibrous retention substrate, (b) a protein-lipid paste, and (c) a liquid. The medium provides nutrients in amounts and proportions effective to support growth of entomophages. In the preferred embodiment, the growth medium mixture is sufficiently blended so that the nutrients are substantially compositionally uniformly distributed.

The adherent, fibrous retention substrate, in addition to providing nutrients to the entomophages, provides a net-like formation, that serves to substantially support or retain the protein-lipid paste. Further, the retention substrate and/or protein-lipid paste, either individually or in combination, substantially retain the liquid. Thus, the growth medium provides a mixture in a stabilized form. The medium mixture has the further advantage that it mimics the structural constituents, texture, and consistency of the natural prey insides.

The growth medium of the invention having a solid/semi-solid form, is more convenient to use than liquid media in terms of packaging and presentation. The medium components are readily available. Further, the medium can be readily packaged, for example in a membrane such as Parafilm®, for presentation to entomophages. Additionally, the growth medium can be readily freeze-dried and reconstituted with liquid with no observable deterioration or loss of nutritional quality. The use of freeze-drying (1yophilization) makes the diet easy to store, ship, or handle. The freeze-dried medium may be stored for months with no loss of nutritional quality.

The growth medium is suitable for rearing entomophages, and finds particular usefulness for the mass rearing of entomophages at a reasonable cost for subsequent use as biological control agents.

As shown by the data, given below, the new diet produces results superior to those obtained by rearing on factitious prey. Use of this growth medium yields adults that produce more eggs than those reared on factitious prey, and additionally, the entomophages grow faster and larger than when reared on factitious prey, and they are comparable to those reared on natural prey.

Further, as discussed in detail below, the texture, consistency, and composition of the medium is well suited to the insect predators that pre-digest their prey and must recapture their digestive enzymes and digested, liquified medium to complete their digestion.

Additionally, the growth medium of the invention provides an economical means for rearing entomophages. The medium costs about $6.00 per kg including the packaging compared with about $500 per kg for Sitotroga eggs (the factitious host of Chrysoperla spp.), or only about 1/100th the cost. The cost of the medium is about 1/10 the cost for the protein hydrolyzate-based liquid medium (Vanderzant, supra, and Hassan and Hagen, supra) of $50 per kg.

Accordingly, the artificial growth medium of the invention represents a major breakthrough for large-scale production of predatory insects, and has the potential to greatly expand the use of these biocontrol agents in agriculture.

The diet also finds use as a bait and feeding stimulant for entomophages. As shown in the field tests described in Example 4, below, entomophagous ants (fire ants) were attracted and stimulated to feed on the growth medium of the invention, both in the hydrated form and in the freeze-dried form.

The growth medium of the invention is also useful as a supplement for artificial diets for phytophagous pests that are also known to supplement their plant-eating habits with some insect consumption. As shown in Example 5, below, Lygus hesperus reared on a diet which included a plant-based artificial diet in admixture with the growth medium of the invention showed no evidence of population decline or dwindling of size or fecundity of adults.

In accordance with this discovery, it is an object of the invention to provide an improved artificial diet for production of entomophages.

Another object of the invention is the provision of an artificial diet for rearing entomophages which yields high quality predators.

A further object of the invention is the provision of an artificial diet for rearing entomophages which is free of insect components.

An even still further object of the invention is to provide a growth medium for use for economical mass production of entomophages for subsequent release as biological control agents, for example, augmentative releases for control of populations of insect pests in commercial agriculture.

An additional object of the invention is to provide a bait and feeding stimulant for entomophages.

A further object of the invention is to provide a supplement for an artificial diet for phytophagous pests that supplement their plant-eating habits with insect consumption.

Other objects and advantages of the invention will become readily apparent from the ensuing description.

DETAILED DESCRIPTION OF THE INVENTION

The artificial diet or growth medium of the invention is formulated to provide nutrients effective for supporting the growth of larvae of entomophages from the time of hatching until pupation, and also provides nutrients effective for rearing entomophages which have predaceous adult stages. The medium is free from insect components, such as hemolymph, and is suitable for the production of entomophages on a commercial scale at a relatively low cost. Moreover, the entomophages are of sufficient quality to function effectively as biological control agents following release into the field.

As used herein, the term "entomophages" refers to predatory arthropods and parasitic insects (parasitoids). Entomophages are discussed in detail in the text *Entomophagous Insects* by C. P. Clausen, Hafner Publishing Company, New York (1972), which is incorporated herein by reference. Entomophage refers to insects that feed upon other insects. These insects are broadly divided into two general classes, predators and parasitic insects. While there are many instances of species that are intermediate between the two general classes, a parasitic insect, in general, refers to one that, in its larval stage, develops either internally or externally upon a single host individual, the latter eventually dying as a result. The adults are generally free-living, and their food sources are usually distinct from those of the larvae. In contrast, a predator is generally free-living in the larval stage also and requires a number of individuals to provide food to grow to maturity. Clausen, supra, reports that there are 224 families in 15 orders, which to some extent, feed upon other insects.

Entomophages of particular importance to commercial agriculture are those useful as biological control agents, for example, through augmentative releases, to control populations of insect pests on agricultural commodities. Without being limited thereto, exemplary of predatory arthropods having importance for biocontrol in a commercial agricultural setting include predators of the Order (species)/family: Heteroptera: *Geocoris punctipes* (Say)/Lygaeidae [big eyed bug]; *Podisus maculiventris* (Say)/Pentatomidae; *Podisus sagitta* (Fab.)/Pentatomidae; *Macrolophus caliginosus* Wagner/Miridae; Neuroptera: *Chrysoperla carnea* Stephens/Chrysopidae [lacewings]; *Chrysoperla rufilabris* Burmeister [lacewings]; *Chrysopa sinica*/Chrysopidae; *Chrysopa scelestes* Banks/Chrysopidae; *Chrysopa lanata lanata* Banks/Chrysopidae; *Chrysopa septempunctata* Wesmael/Chrysopidae; Coleoptera: *Harmonia axyridis*/Coccinellidae, *Olla abdominalis*/Coccinellidae. Without being limited thereto, exemplary parasitoids having potential importance for biocontrol in a commercial agricultural setting include Hymenoptera, in particular, Trichogrammatidae; Braconidae, and Ichneumonidae; and Diptera, in particular, Tachinidae. Without being limited thereto, exemplary entomophagous ants having potential importance in a commercial agricultural setting include Hymenoptera, Formicidae: Solenopsis (fire ants), in particular, *Solenopsis*

*invicta* (red imported fire ant), *Solenopsis geminata*, and *Solenopsis richteri* (black imported fire ant) and Hymenoptera, Formicidae: Camponotus (carpenter ants).

Growth Medium

The growth medium of the invention is composed of a mixture of (a) an adherent, fibrous retention substrate, (b) a protein-lipid paste, and (c) a liquid, the mixture having nutrients in amounts and proportions effective to support growth of the entomophage being reared (target entomophage).

(a) Adherent. Fibrous Retention Substrate.

A critical feature of the growth medium of the invention is the inclusion of an adherent, fibrous retention substrate or reticulum that, in addition to providing nutrients for growth of the target entomophage, provides a net-like formation which substantially supports or retains the protein-lipid paste. Further, the retention substrate and/or protein-lipid paste, either individually or in combination, substantially retains the liquid.

The adherent, fibrous retention substrate is sufficiently solid to support or hold the other components in the medium. Further, the substrate has an adherent or sticky character and a fibrous or stringy net-like character (including discontinuous network sections and fibers), to substantially retain the protein-lipid paste and liquid, and the nutrients therein, thereby providing the growth medium in stabilized form. Without being limited thereto, the retention of the nutrients by the adherent fibrous retention substrate can be (a) by physical entrapment or capture within the adherent, fibrous retention substrate, (b) by physical-chemical means, for example, through hydrophilic or lipophilic interactions or protein-protein interactions of the network or portions thereof with the protein-lipid paste or water, or nutrients therein, (c) by formation of lipoprotein complexes, (d) by components having natural cellular "glues" such as proteoglycans, (e) or any combination of the foregoing. Thus, the adherent, fibrous retention substrate functions effectively as a net-like substrate or reticulum to substantially retain nutrients in the growth medium in a stable form.

Preparation of an adherent, fibrous reticulum suitable for the growth medium of the invention can be conveniently accomplished by treating whole, blended egg in a manner to produce a sticky, stringy network. As described in Example 1, below, this can be conveniently carried out by putting blended whole egg through an instantaneous or flash heating process such as by dispersing it in a hot liquid to thereby produce a sticky, stringy network. Other forms of heating of the whole blended egg can be used which provide a sticky, stringy net-like formation which retains nutrients in the growth medium.

Blended whole egg is advantageous for several reasons, including the following: (a) it provides the "stickiness" useful to hold or retain medium components and nutrients, (b) the egg white provides proteins including albumin that can provide a stringy quality, (c) the egg yoke provides an excellent natural source of cholesterol, lipids, lipoproteins, protein, and B-vitamins, (d) egg has hydrophilic and hydrophobic properties, and can retain nutrients by lipid-lipid interactions, protein-protein interactions, hydrophilic interactions, and by the formation of lipoprotein complexes, (e) whole egg that is blended and cooked provides a concentrated amount of important nutrients such as cholesterol that do not separate during further handling of the medium, and the heating denatures avidin which otherwise binds biotin, an essential water soluble vitamin, and (f) it may provide proteoglycans to act as natural cellular adherent materials.

As discussed in detail below, the fibrous, adherent retention substrate provides a further advantage when the growth medium is used for rearing insect predators that pre-digest their prey and must recapture their digestive enzymes and ingest the digested, liquified medium to complete their digestion (extra-oral digestion). This is because the fibrous, adherent retention substrate substantially retains the digestive enzymes exported by these entomophages for a time sufficient for digestion of the growth medium and for recapture of the digestive enzymes and ingestion of the liquified medium by the insect.

(b) Protein-lipid Paste.

The protein-lipid paste component of the growth medium of the invention provides a protein-lipid composition which provides important nutrients to support growth of the target entomophage in a form suitable for retention by the adherent, stringy reticulum. The paste has sufficient consistency to be retained when mixed together with the adherent, fibrous reticulum and water components of the growth medium. As discussed above, retention includes physical chemical interactions, including lipid-lipid interactions, protein-protein interactions, and formation of lipoproteins complexes of the lipid-protein paste and adherent, fibrous retention substrate.

A further aspect of the protein-lipid paste is that it provides a composition rich in proteins and lipids. The amounts and concentrations of proteins and lipids to be provided by the total growth medium are discussed in detail, below.

As shown in Example 1, below, the protein-lipid paste can be conveniently prepared by blending together ground beef and beef liver. Exemplary of other sources suitable for preparation of the protein-lipid paste include fish innards, oysters, meat and liver from other animals, such as chicken, lamb, and pork, and cells derived from animals including insects and propagated and multiplied using cloning technology as known to those of skill in the art.

(b) Liquid.

The liquid component of the medium can comprise water, or other sources of water such as milk or medium from tissue culture, and may include additional water soluble nutrients or additives such as vitamins, minerals, antimicrobial agents, or preservatives. The liquid may be added together with the reticulum and may be blended together with the ground beef and beef liver to achieve a protein-lipid paste having the desired final consistency as described in Example 1, below. The liquid functions to support growth of an entomophage, and further, in the case of entomophages that feed using extra-oral digestion, provides liquid for entomophages to pre-digest their food.

Preparation of the Growth Medium

The medium is prepared in a manner to effect the substantial capture/retention of the nutrients in a stable form, that is, wherein the nutrients effective to support growth of an entomophage are substantially retained in the medium. The retention substrate, paste, and liquid are sufficiently blended together to form a stable medium. In the preferred embodiment, the substrate, paste, and liquid are intimately or thoroughly mixed so that the nutrients are compositionally uniform in the growth medium, that is, wherein the nutrients for effective growth of the target entomophage are in its feeding zone, e.g., an area within reach of the insect's mouthparts and/or mouthparts and forelegs. The feeding zone of an entomophage can vary among species. For larger entomophages, it can be about a 3 mm×3 mm area. For smaller entomophages such as Chrysoperla, the feeding zone can be about a 100 $\mu$m×100 $\mu$m area.

An exemplary formulation is prepared by mixing together adherent, fibrous cooked whole blended (e.g., flash-heated blended whole egg that has a sticky and stringy character), water, and a ground beef-beef liver paste to achieve a substantially compositionally uniform mixture (see Example 1, below).

The growth medium can be readily freeze-dried using procedures known in the art and reconstituted (rehydrated) with liquid with no observable deterioration or loss of nutritional quality. The use of freeze-drying (lyophilization) makes the diet easy to store, ship, or handle. The freeze-dried product may be stored for months with no loss of nutritional quality.

Growth Medium Mixture

The growth medium provides a mixture in a stabilized form, and has the further advantage that it mimics the structural constituents, texture, and consistency of the natural prey insides.

The growth medium mixture prepared as described in Example 1, below, includes solid and semi-solid areas and interstitial liquid. Observing the mixture macroscopically, it looks like a fibrous, paste-like mixture that has body. It is "wet" but not runny, and has a homogenous "coffee with cream" color. In these aspects it parallels the texture and consistency of the insides of the natural prey, e.g., muscles, fat body, reproductive organs, etc., after the predator has sucked out the hemolymph, that is, a pasty material with some stringy stuff in it. Microscopically, it appears, in general, to have spherical particles in the range of about 1–10 $\mu$m and composed largely of lipoprotein complex (observed by staining), and "fibers" in the range of about 10–80 $\mu$m diameter and about 50–200 $\mu$m in length. The fibers may be composed of smaller particles. The mixture was compositionally uniform, that is, the fibers and particles were present in a 100×100 $\mu$m area of diet.

Nutrients in the Growth Medium

The growth medium provides nutrients in amounts and proportions effective to support growth of the target entomophage. The medium should contain essential nutrients. Essential nutrients are defined as those nutrients such as minerals, amino acids, cholesterol, fatty acids, lipid soluble vitamins, and water soluble vitamins that are essential to the growth of the target entomophage. The basic nutritional requirements of parasitoids and predators for an artificial growth medium are discussed in Grenier et al., supra, which is incorporated herein by reference. As known to those in the art, nutrients essential for growth of an entomophage can vary among species. For any particular entomophage species, nutrients essential for growth can readily be determined by procedures known to those of skill in the art, for example, dietary deletion. The actual concentrations selected may be determined by the practitioner skilled in the art. In general, the absolute amount of the protein in the growth medium, that is, the combined amount of all protein in the medium should be between approximately 12 to 22% of growth medium (total wet weight), the absolute amount of the lipid should be between about 10–20% of the growth medium (total wet weight), the absolute amount of cholesterol should be in the range of approximately 1000–3000 mg per kg growth medium and the absolute amount of water in the growth medium (including added water and water contained in the other ingredients) should be in the range of 50–70% of the growth medium (total wet weight). The lipid and protein sources may be provided in combination such as by lipoproteins. Preferably, at least 20% of the lipids should be triglycerides and they can range up to 90%; at least 5%, and up to 50% of the lipids, should be phospholipids (polar lipids). For rearing Chrysoperla, it is recommended that the growth medium contain 17–21% protein (wet weight), 15–19% lipid (wet weight), 2000–3000 mg cholesterol per kg diet, and 55–65% water (wet weight). A preferred composition for rearing Chrysoperla includes about 19% protein (wet weight), 17% lipid (wet weight), 2500 mg cholesterol per kg diet, and 60% water (from all sources).

For optimum growth, a diet that parallels the composition of nutrients in the natural prey is suggested. This can be determined by protein hydrolysis and subsequent amino acid analysis, gas-liquid or liquid chromatography of lipids, microbial bioassay of vitamins, atomic absorption spectrophotometry for minerals, and overall bioassay with insect subjects.

The growth medium of the invention with its uniquely high protein, lipid and cholesterol concentrations compared to prior art liquid diets, and the unique capturing and stabilizing of these components provides an ideal combination of the nutrients and the form in which these nutrients are best utilized. The invention provides a completely new means of feeding entomophages. It is particularly useful for feeding *C. Carnea* and *C. rufilabris* and other predatory insects with similar feeding habits, i.e., that feed by a process of extra-oral digestion. It provides a very nutrient-rich mixture of dietary components, especially lipids, including unsaturated fatty acids, sterols, and lipid soluble vitamins without separation of these components and their loss from the available "nutrient pool." *C. carnea* and *C. rufilabris*, reared on this growth medium exhibit increased pupal weight, fecundity (number of eggs produced per adult female), and net reproductive rate in comparison with those produced on the artificial diets of the prior art. These results are particularly unanticipated in view of the fact that efforts to rear Chrysoperla using a meat-based diet (Cohen, 1985, supra) were unsuccessful. The insects did not complete development on the latter diet.

Other adjuvants or supplements may also be incorporated into the medium to enhance the growth of the target entomophage or prevent the growth of microbial contaminants. For example, the growth medium may also include non-essential nutrients, for example, carbohydrates, lipids, amino acids, and nucleic acids that are not essential for growth, but are useful as energy, nitrogen, and carbon sources, but can be manufactured in the metabolic pathways of the predators. The non-essential nutrients may also have important metabolic and behavior-inducing characteristics, such as phagostimulatory nutrients, that is, an ingredient that stimulates the target insect to stimulate the complete feeding response. Exemplary of phagostimulant sources are sucrose, honey, tryptophan, and gamma amino butyric acid.

Sources of carbohydrates for use in the growth medium include sucrose, glycogen, glucose, and others as known to those of skill in the art.

Vitamins, in particular B-vitamins, in the medium may be supplemented by adding brewer's yeast to the growth medium. Brewer's yeast is also a source of nitrogen, amino acids, and trace elements.

I have surprisingly found that antimicrobial agents may be included in the diet. This is in contrast to prior teachings that the growth of entomophages would be negatively affected by the inclusion of antimicrobial agents in the growth medium. The addition of an antimicrobial agent to the medium is advantageous because it prevents spoilage by bacteria and fungi and thus allows extension of the "cage-life" of entomophages, from about 1.5 days to 3–4 days. This means that under commercial production circumstances, the medium can be changed less frequently than medium without the inclusion of antimicrobial agents, thereby resulting in a great savings in labor costs.

Without being limited thereto, exemplary of such antimicrobial agents are propionate, potassium sorbate, streptomycin, and chlortetracycline. The antimicrobial agents are included, individually or in combination, in an amount sufficient to prevent growth of microbial contaminants, but insufficient to prevent growth of the target entomophage. I have found that the antimicrobial agents can be tolerated by the predatory insects *C. carnea, Geocoris punctipes, Orius insidiosus* and *Serrangiwm parcesetosum* with no loss of survival, weight, fecundity or fertility.

The pH of the growth medium can range from about 5.5 to 9. It is recommended that the pH of the growth medium be in the range of approximately pH 6 to 7. The optimal range is about 6.3 to 6.7, and preferably 6.5. The pH can be conveniently adjusted using a solution of acetic acid or potassium hydroxide.

A growth medium of the invention which provides nutrients for rearing the green lacewing, Chrysoperla, is set forth in Example 1, below. Chrysoperla is a highly praised generalist predator. It has been well documented that Chrysoperla suppresses populations of aphids, lepidopterans (eggs and small larvae), and a variety of other slow or non-moving, soft bodied arthropods. This entomophage meets the criteria for use as a biocontrol agent such as high kill rates, good search qualities, and proven non-destructiveness to other beneficial arthropods and crop plants. Chrysoperla spp., especially *C. carnea* and *C. rufilabris*, are sold by numerous producers and suppliers to control pests in agricultural settings of limited scope such as in greenhouses and small plots of high cash crops. However, the commercially available Chrysoperla spp. are all produced on factitious hosts such as the eggs of *Sitotroga cerealella* (O.) (Lepidoptera: Tineidae) or *Ephestia kuehniella* (Z.) (Lepidoptera: Phycitidae), making *C. carnea* and *C. rufilabris* too expensive for use to control pests in large scale, open field-type agricultural settings. Considerable progress has been made in the manipulations of Chrysoperla spp. colonies for augmentative purposes. There are several reports of artificial media developed for Chrysoperla spp. (Grenier et al., 1994, supra). However, none of these media have been incorporated into the augmentative production systems for these predators.

Use of the growth medium of the invention to rear Chrysoperla yielded predatory insects of unexpectedly superior quality than attainable using previously disclosed artificial diets and the factitious host, Sitotroga eggs. Over forty successive generations of *Chrysoperla rufilabris* and five successive generations of *Chrysoperla carnea* have been produced using the artificial medium of the invention for larval development and a yeast/honey mixture for adults. Fecundity and fertility were nearly identical in artificial medium-produced Chrysoperla and those produced on a factitious host (Sitotroga eggs). The predators were larger and faster developing than counterparts reared on Sitotroga eggs. Larvae from eggs produced by medium-fed adults readily attacked and consumed cotton aphids, *Aphis gossipyi* (Homoptera: Aphididae), and the eggs and larvae of several species of lepidopteran cotton pests (pink bollworm, tobacco budworm, and cabbage loopers).

In the growth medium described in Example 1, below, essential nutrients were provided by egg, ground beef, beef liver, and water. Other nutrients and additives included brewer's yeast, sugar, honey, acetic acid solution, and antimicrobial agents. In brief, the growth medium was prepared using blended whole egg to form the adherent, fibrous substrate or reticulum, and as a natural source of protein and lipid, including cholesterol. The protein-lipid paste was prepared using fatty ground beef and beef liver, which also provided natural sources of protein and lipid. The liquid used was water. The whole egg was treated with a flash-heating technique and immediately mixed with the blended meat, thereby causing the capture of the nutrients in a solid, stable form that simulates the structural constituents, texture, and consistency of the natural prey insides.

The medium has the full nutrient compliment of lipids bound with the proteins and other nutrients and stabilized with heat and with natural cellular "glues" such as glycans. This medium has nearly an identical texture and chemical profile with natural prey insides and allows the predators to undergo their natural feeding strategies of extra-oral digestion as discussed in detail below, and pre-oral selection of required nutrients, leaving behind undesirable or non-useful substances.

In addition to *C. rufilabris* and *C. carnea*, 5 generations of *Geocorts punctipes*, 3 generations of *Serangium parcesetosum*, and 3 generations of *Orius insidiosus* have been reared on this diet. Adults have also been produced on this diet, one generation, of *Perillus bioculatus* and *Podisus maculiventris* (which are both predatory stink bugs in the family Pentatomidae and which are both of great economic potential). Additionally, in laboratory experiments, imported fire ants (*Solenopsis invicta*) reared on the growth media of the invention showed increased colony biomass at a rate only slightly less than colonies provided with their natural food source, crickets. The cost of rearing fire ants on the natural food source (crickets) is prohibitively expensive for large scale feeding; the medium of the invention provides an economical means for mass rearing of entomophagous ants.

The novel composition and texture of the growth medium of the invention allows natural feeding behavior of entomophages. The growth medium of the invention utilizes physical and dietary needs of the entomophages, as well as behavioral characteristics, to maximize rearing of entomophages, and obtaining entomophages of superior quality. The texture, consistency, and composition of the medium is well suited to the entomophages that pre-digest their prey and must recapture their digestive enzymes and ingest digested, liquified medium to complete their digestion. It has been reported that at least 79% of predaceous land-dwelling arthropods use extra-oral digestion, a process wherein an entomophage exports a complex of digestive enzymes outside of its body, digests the prey by digestive liquefaction of prey solids and reduction of viscosity of intractable liquids, and subsequently ingests the liquified material (nutrient-rich slurry) and recaptures its digestive enzymes (A. C. Cohen (*Annu. Rev. Entomol.* 40:85–103 (1995)). The cycle is repeated so that the liquefaction and removal of prey contents are incremental. An important aspect is the recovery of both the prey contents and the digestive enzymes that were invested in the prey because disgorged digestive enzymes are important to complete digestion of the prey once they are reingested, loss of the enzymes means forfeiture of nutrients because they are mixed with liquified prey contents, and digestive secretions represent a significant portion of the predator's total protein pool (Cohen, 1995, supra). The reference notes that recovery of disgorged enzymes varies, and can range from over 70% to less than 50%.

The growth medium of the invention which has a solid interspersed with semi-solids which further have some interspersed liquid, mimics the natural consistency of the prey's internal structures and chemistry. I have surprising found that the growth medium of the invention has the unique property of retaining the digestive enzymes exported by an entomophage for a time sufficient for digestion of the growth medium and for recapture of the digestive enzymes and ingestion of liquified medium by the insect, in an amount effective to support growth of the entomophage. This is because the medium is prepared of components which capture of the nutrients in a solid, stable form, and provide nutrients effective to support growth of the entomophage. In the case of insects that use extra-oral digestion, it is preferred that the growth medium retain the digestive enzymes and digested, liquified medium within the feeding zone of the entomophage for a time sufficient for the predator to recapture the enzymes and ingest the growth medium digested by the enzymes in an amount effective to support growth of the entomophage. In general, this is at least about 30 seconds. The "feeding zone" of an entomophage that feeds by a process of extra-oral digestion, is the space that is reachable by its mouthparts. For example, the feeding zone for the first instar Chrysoperla is about 10 to 20 $\mu$l volume. The feeding zone for other entomophages can be readily determined by the gape or size of their mouthparts.

The other 20% of the predatory arthropods feed by chewing and piecemeal mechanism. Piecemeal feeding means that the insect breaks off pieces of the prey either with its mouthparts or forelegs, and then it ingests the smaller pieces. The diet or growth medium of the present invention is also excellent for feeding insects that feed in this manner, because it is much more accommodating to the solid feeding mechanism of the predator than a liquid diet. The feeding zone for these predators is the space reachable by the insect's mouthparts and forelegs. Serangiun Coccinellidae, both larvae and adults, reared on the growth medium of the invention completed development and reproduced.

The medium can be readily packaged, for example, in a membrane such as Parafilm® (a flexible, moldable, self-sealing, odorless, moisture resistant, thermoplastic, semi-transparent, and practically colorless membrane), and be presented to the entomophages in a shape and wall thickness that simulates natural prey. The packaged medium can be sterilized and will remain sterile for subsequent use for rearing the target entomophage.

The growth medium can be readily freeze dried and reconstituted with liquid using procedures known in the art with no observable deterioration or loss of nutritional quality. The use of freeze drying (lyophilization) makes the diet easier to store, ship, or handle. As described in Example 3, below, freeze drying makes it possible to store the diet at room temperature for 6 months with no loss of nutritional quality or feeding stimulation.

Techniques for rearing larvae of entomophages in vitro on artificial diets have been described by Cohen et al., 1985, supra, which is incorporated herein by reference. In brief, eggs or larvae are provided with the growth medium in an amount effective to support growth, and incubated under conditions and for a period of time for the eggs or larvae to mature into pupae or adults. In accordance with the preferred embodiment, the growth medium is presented in a suitable container such as a petri dish or multicell container. Organdy may be used to enclose cells to permit air flow and prevent escapes. Because of the mobility of first and second instar larvae and their predisposition for cannibalism, multi-cell or other compartmentalized containers are preferred to segregate developing larvae. The cells and/or diet may be covered with a membrane. The membrane covers may be formed from a variety of polymeric materials, including but not limited to paraffin, polyethylene, polypropylene, and Parafilm®. Use of Parafilm® as a cover is particularly advantageous as this membrane may serve as a phagostimulant, and it keeps the diet from drying out and from being accessed by microbes. I have found that presentation of the medium in stretched Parafilms® membrane is advantageous for the smaller predators so the mouthparts of the insect can readily penetrate the Paraffime®.

Entomophages which have predaceous adult stages may be reared on the diet of the invention. Other adults may be fed on brewer's yeast, honey, and water, as known to those of skill in the art.

Use as a Bait. The growth medium of the invention is an excellent bait and feeding stimulant for entomophages, both in the hydrated form and freeze-dried form. When used as a bait, an effective bait amount of the growth medium is provided in an area where entomophages are to be baited, that is, an area frequented by the target entomophages; an area where the target entomophages may forage for food or otherwise occur; or selected areas where detecting, and/or controlling of these pests is desired. As shown in the field tests described in Example 4, below, the growth medium of the invention is useful as a bait for entomophagous ants (*Solenopsis invicta*). The ants were attracted and stimulated to feed on the growth medium in the hydrated form and in the freeze-dried form.

The growth media may be used as a bait in combination with a control agent for entomophages as known in the art, including toxicants, pesticides, chemosterilants, pathogens, or insect growth regulators. For example, the growth media may be used in combination with a toxicant to provide a poisoned bait.

The growth media bait may be optionally combined with other materials that attract or stimulate feeding of entomophages; that serve as carriers or extenders, or that aid in the capture and killing of lured entomophages as known in the art.

Use in the Artificial Diet of Phytophages that Supplement Their Plant-Eating Habits with Insect Consumption The growth medium of the invention is useful as a supplement in the artificial diet for phytophagous (plant-eating) pests that display some insect consumption in addition to eating plants. Without being limited hereto, exemplary of predominantly phytophagous insects include Heteroptera: Miridae: Lygus spp., for example, *Lygus hesperus* Knight. Lygus spp. are known to be important pests in several cropping systems (seed alfalfa, cotton, strawberries, orchard crops). They are also known to supplement their plant-eating habits with some insect consumption. This fact (their facultative entomophagy) sets the stage for using the growth medium of the invention as a supplement in the artificial diet-based production of parasites of Lygus bugs. The diet is prepared by mixing together a plant-based diet (97–80%) of phytophagous insects with 3–20% (by weight) of the growth medium of the invention.

Example 5, below, describes the rearing of Lygus on a plant-derived diet (which includes lima bean meal, wheat germ, soy flour) supplemented with the growth medium of the invention. Seven continuous generations of *L. hesperus* were produced on the diet with no evidence of population decline or dwindling of size or fecundity of adults.

EXAMPLES

The following examples are intended only to further illustrate the invention and are not intended to limit the scope of the invention which is defined by the claims.

Example 1

This example describes an artificial medium and its use for rearing larvae of the green lacewing, Chrysoperla.

Materials and Methods:

Insects and cages: Eggs of *Chrysoperla rufilabris* Burmeister (Neuroptera: Chrysopidae) used to start cultures were obtained commercially (Biofac, Mathis, TX). Newly hatched larvae were either placed individually in Petri dishes or in Verticele® (multicell container made of cardboard) cells (ca. 4×6×12 mm or about a 400µl capacity). The Chrysoperla in Petri dishes were provided with a packet of medium in Parafilme® (American Can Co., Marathon Products, Neenah, Wis.) that measured about 1×1×0.5 cm and contained approximately 0.5 g of medium per insect. The stretched Parafilm® was about 15–20 µm thick. Chrysoperla in the Verticel® cells were presented with medium packets that were placed above an organdy top that was glued to the cells. The cells were further enclosed by a second piece of organdy that was glued to the bottom to permit air flow and prevent escapes. The organdy cloth had openings that were about 230×200 µm, and the fibers were about 100 µm thick. The rearing conditions were 27° C., Relative Humidity (R.H.) of 40–50%, and 14 hours light: 10 hours darkness.

Medium Preparation: The medium was prepared as follows. A protein-lipid semi-solid paste was prepared using the following ingredients: 100 g ground beef (with 30% fat), 100 g beef liver, 10 g brewer's yeast (ICN Catalog #903312, 39% protein, 5% ash, fat minimum 0.5%, fiber maximum 8%), 5 g honey, and 20 ml water (filtered through a Millipore filter). The beef liver, ground beef, brewer's yeast, honey, and water were blended for 3 minutes in a Cuisinar® food processor to obtain a protein-lipid paste.

The adherent, fibrous retention substrate was prepared as follows. In a 4000 ml beaker, 45 ml water (filtered thorough a Millipore filter), 5 ml acetic acid solution (10%:90% water), and antimicrobial agents composed of 0.6 g propionate, 0.6 g potassium sorbate, 0.1 g streptomycin, and 0.1 g chlortetracycline were added and stirred until well mixed using a Teflon® coated stir bar with heat. Sucrose (15 g) was added to the solution and stirred until mixed. The sugar solution was heated to near boiling (ca. 85° C.), and 100 g whole blended hen's egg added to the hot (ca. 85° C.) solution, with constant stirring until the egg gelled but was not over-cooked to complete hardness. The egg was "solid" but sticky and stringy at this point.

The heated egg and water mixture was added to the protein-lipid paste in the Cuisinart® food processor and blended until the ingredients were thoroughly mixed (approximately 3–5 minutes). The growth medium contained approximately 19% protein and 17% lipid including about 2500 mg of cholesterol (whole egg and ground beef, and beef liver) per kg of diet, and 65 g added water in a total of 400 g of diet (approx. 60% total water). The pH was 6.5±0.1. With a spoon, the medium was rationed into aliquots of about 50 g and placed into Baggies® (plastic storage bags) to be used for medium packet preparation or frozen until required.

Adult feeding and handling: After eclosion of adults from their puparia, Chrysoperla were placed collectively into three-liter cylindrical cardboard cartons covered with organdy cloth. A sponge with free water, placed in an 11 cm diameter Petri dish was provided, and food slurry consisting of brewer's yeast, honey, and water (1:1:1 g of each). Adults were fed every other day, and eggs collected daily.

For comparison purposes *C. rufilabris* were reared on the factitious host, Sitotroga eggs as follows: 200 mg of Sitotroga eggs were placed in a 4 cm diameter Petri dish with *C. rufilabris* larvae (first instars).

Results.

Chrysoperla reared individually in Petri dishes had hatch rates above 90% for both medium-reared and Sitotroga-reared eggs. Seventy-four percent of the Sitotroga-fed larvae and 82% of the medium-fed larvae became pupae. Pupae reared on Sitotroga eggs weighed 7.02 (±0.18, S.E. (standard error)) mg, and those reared on the artificial medium of the invention weighed 9.70 (±0.28) mg. Thus far, 12 continuous generations of Chrysoperla have reared on the artificial medium of the invention with no loss of colony vigor.

Chrysoperla reared collectively in Verticel® had a mean pupal weight from the medium without antibiotics of 10.09 (±1.24, S.E.) mg and a mean pupal weight for those reared with antibiotics of 10.41 (±0.98) mg. Pupae from the Sitotroga treatment were 7.55 (±1.15, S.E.) mg. Complete larval development times were 11.2 (±0.68) and 10.52 (±0.85) days for treatments without and with antibiotics. Larval development took 12.2 (±1.66) days for larvae fed Sitotroga eggs.

Thus far, over 40 continuous generations of *C. rufilabris* have been produced on the artificial medium. Individuals from the first 15 generations were provided with cotton aphids, *Aphis gossipyi* (Homoptera: Aphididae). They demonstrated apparently normal, voracious feeding. When both feeding packets with artificial medium were presented to lacewing larvae, the predators showed a distinct preference for the aphids rather than the artificial medium.

The medium described above costs about $6.00 (U.S.) per kg compared with about $500 per kg for Sitotroga eggs and about $50.00 per kg for protein hydrolyzate-based liquid media. Thus, the media of the invention provides an economical means for mass rearing of entomophages.

Example 2

Using the medium described in Example 1, additional entomophages were reared with the following results: 5 generations of *Geocoris punctipes* (average yield >90%, development time, 40 days from egg to adult), 3 generations of *Serangium parcesetosum* (average yield >70%, under 20 days development time), and 3 generations of *Orius insidiosus* (average yield >80%, 9 days development time). Adults of these species have been produced that developed from eggs to adults: *Perillus bioculatus* (approx. 65% yield, 35 days development time) and *Podisus maculiventris* (approx. 70% yield, 30–35 days development time).

Example 3

The following example describes experiments wherein larvae of the green lacewing, Chrysoperla, were reared on the growth medium of the invention that had been freshly prepared or freeze-dried and reconstituted (freshly or after storage).

Materials and Methods:

The experiment was set up as three treatments: (1) Control, with growth medium that was not freeze-dried, but was used after being freshly prepared; (2) Freshly reconstituted freeze-dried growth medium, and (3) Freeze-dried growth medium that was stored at room temperature 6 months prior to reconstitution.

The insects and cages were as described in Example 1, above. The Control medium was prepared as described in Example 1, above. The Freshly reconstituted freeze-dried growth medium was prepared the same as the Control medium, and was then it was frozen at −70° C. in aliquots of 100 g in glass Virtis freeze-dry flasks. Flasks were connected to a Virtis Freeze Drier where samples were taken to complete dryness (35 g of material remained) over a 20 h period under a vacuum and −45° C. It was reconstituted by adding 65 ml of distilled water and mixing. The stored, freeze-dried growth medium was prepared the same as for the Control, was freeze-dried as described above, and was stored for 6 months at room temperature (23° C. ±2° C.) prior to reconstitution.

Reconstitution was carried out as described above.

In all cases, the diet was placed in stretched Parafilm® packets and presented to Chrysoperla larvae in feeding units as described in Example 1.

Results.

The pupae weighed about 10 mg each in all three treatments. Larval development period was about 12 days for each treatment, and pupal period was about 10 days, indicating that there was no apparent loss of dietary quality, nutritional efficacy or feeding stimulation resulting from freeze-drying or from prolonged storage of the freeze-dried product. Also, there was no observable deterioration of the freeze-dried product that was freshly reconstituted or stored and reconstituted.

Example 4

The following example describes field studies wherein the growth medium of the invention in fresh form or freeze-dried, non-reconstituted form, is used as a bait for entomophagous ants.

Materials and Methods: The growth medium was prepared as described in Example 1 except that antimicrobial agents were not added. The freeze-dried, non-reconstituted growth medium was described as in Example 3 except that antimicrobial agents were not added.

The growth medium in fresh form or freeze-dried, non-reconstituted form was placed in Parafilm® packets, and the packets were set near active *Solenopsis invicta* (red imported fire ant) mounds. After 24 h, the packets were examined for evidence of fire ant activity (removal of diet).

Results. All packets had fire ants on them with clear evidence of diet removal by the ants. This demonstrates the usefulness of the growth medium of the invention as a bait and feeding stimulant.

Example 5

The following example illustrates the use of the artificial media as a supplement for an artificial diet for Phytophages which supplement their plant-eating habits with insect consumption.

Materials and Methods:

Eggs of *Lygus hesperus* Knight (Heteroptera: Miridae) were obtained. The artificial diet for *Lygus hesperus* was prepared by combining the growth medium as described in Example 1 without antimicrobial agents with plant-derived components (consisting of 300 g of lima bean meal, 200 g of wheat germ, 200 g of soy flour, 1 g of vitamin mixture, 700 ml water and 0.1% formalin). The plant-derived components and growth medium of Example 1 were each prepared separately and combined: 10% by weight of the growth medium of Example 1 and 90% by the plant-derived diet. Lygus bugs were reared on the combination artificial diet as follows: the combination diet was sealed in unstretched Parafilm® packets and placed on top of screen covering the cages of *Lygus hesperus* that had recently hatched from eggs.

Results.

Seven continuous generations of *Lygus hesperus* were produced on the combination diet with no evidence of population decline or dwindling of size or fecundity of adults.

It is understood that the foregoing detailed description is given merely by way of illustration and that modifications and variations may be made therein without departing from the spirit and scope of the invention.

What is claimed is:

1. A freeze-dried product which comprises a growth medium for providing nutrients for rearing an entomophage, comprising a mixture of (a) cooked whole egg, (b) a protein-lipid paste, and (c) a liquid, wherein said cooked whole egg forms a sticky, stringy substrate that substantially retains nutrients in said protein-lipid paste in stable form, and wherein said nutrients are present in amounts and proportions effective to support growth of an entomophage, wherein said mixture is freeze-dried.

2. The freeze-dried product of claim 1 which is reconstituted subsequent to freeze-drying.

3. The freeze-dried product of claim 1, wherein said protein-lipid paste comprises a mixture of ground beef and beef liver.

4. A method for baiting entomophages, which comprises placing in an area where entomophages are to be baited, a nutrient mixture comprising (a) cooked whole egg, (b) a protein-lipid paste, and (c) a liquid, wherein said cooked whole egg forms a sticky, stringy substrate that substantially retains nutrients in said protein-lipid paste in stable form, and wherein said nutrients in said nutrient mixture are present in amounts and proportions effective to support growth of an entomophage.

5. The method of claim 4 wherein said mixture is freeze-dried.

6. The method of claim 4 wherein said entomophage is an entomophagous ant selected from the group consisting of *Solenopsis invicta*, *Solenopsis geminata*, and *Solenopsis richteri*.

7. The method of claim 4 wherein said entomophage is an entomophagous ant of the genus Camponotus.

8. The method of claim 4 wherein said bait is in combination with a control agent for said entomophage.

9. An artificial diet for rearing phytophagous insects which consume insects in addition to plants, which comprises 97–80% by weight of a plant-based phytophagous artificial diet in admixture with 3–20% by weight of a growth medium comprising a nutrient mixture comprising (a) cooked whole egg, (b) a protein-lipid paste, and (c) a liquid, wherein said cooked whole egg forms a sticky, stringy substrate that substantially retains nutrients in said protein-lipid paste in stable form.

10. A method for rearing a phytophagous insect which consumes insects in addition to plants, comprising providing eggs or larvae of said phytophage with the artificial diet of claim 9 and incubating under conditions and for a period of time effective to allow said eggs or larvae to mature into pupae or adults.

* * * * *